United States Patent [19]

Tanaka et al.

[11] 4,242,277

[45] Dec. 30, 1980

[54] NITROSATION PROCESS

[75] Inventors: Morihisa Tanaka; Kazuhiko Konno; Norio Sasaki; Kunio Uchimura, all of Ami, Japan

[73] Assignee: Mitsubishi Petrochemical Company, Limited, Tokyo, Japan

[21] Appl. No.: 43,905

[22] Filed: May 30, 1979

[30] Foreign Application Priority Data

Jun. 5, 1978 [JP] Japan ................................. 53/67447

[51] Int. Cl.$^3$ ..................... C07C 131/00; C07C 87/60
[52] U.S. Cl. .................................. 260/396; 564/265; 564/267; 564/441
[58] Field of Search .................. 260/577, 590 R, 647, 260/566 A; 568/706, 709

[56] References Cited

PUBLICATIONS

Hodgson et al., "J. Chem. Soc.", p. 1808 (1939).
Organic Syntheses, Coll. vol. 1, p. 511.
Justus Liebig's Annalen der Chemie, vol. 277, p. 85.
J. Chem. Soc., p. 1677 (1955).
Organic Syntheses, Coll. vol. 2, p. 223.

*Primary Examiner*—John Doll
*Attorney, Agent, or Firm*—Oblon, Fisher, Spivak, McClelland & Maier

[57] ABSTRACT

In the process of subjecting a compound selected from phenols, N,N-dialkylanilines and mixtures thereof to nitrosation reaction conditions using a nitrite in an aqueous system to prepare nitrosated products selected from benzoquinone oximes and p-nitroso-N,N-dialkylanilines, the nitrosation reaction is advantageously carried out in the presence of an acid stronger than nitrous acid an organic acid of pKa 2 to pKa 5 or a salt thereof and water, the quantities of the organic acid and water being up to 5 times by mole and up to 10 times by weight the quantity of the compound to be nitrosated, respectively.

11 Claims, No Drawings

4,242,277

NITROSATION PROCESS

BACKGROUND OF THE INVENTION

1. Field of the Invention

This invention relates to a process for nitrosation of a compound selected from phenols and N,N-dialkylanilines to prepare the corresponding benzoquinone oximes or p-nitroso-N,N-dialkylanilines.

The standard processes for preparation of these nitrosated products comprise subjecting a phenol or a dialkylaniline to nitrosation reaction conditions using a nitrite ion in an aqueous system, wherein an acid stronger than nitrous acid acts on the nitrite to produce nitrous acid. The resulting nitrous acid is the actual nitrosating agent. In this connection, the process can be one of using nitrous acid itself instead of forming it "in situ" from a nitrite ion and a mineral acid, but this process is generally not practicable because of instability of the aqueous nitrous acid and the like.

Various methods have been used for carrying out such nitrosation reactions. From the industrial viewpoint, however, all conventional methods involve some problems or are otherwise not fully satisfactory.

2. Prior Art

The following processes are illustrative of representative conventional processes.

(1) Acetic acid solvent process (J. Chem. Soc. 1939 1808)

This process comprises dissolving the starting phenol in a large amount (about 13-fold excess) of aqueous 50% acetic acid solution, and causing an aqueous solution of nitrite ion to act thereon. The reaction in such a dilute system gives rise to problems such as those relating to the efficiency per volume of reactors, the isolation and recovery of products, the recovery of the acetic acid used, and the losses upon recovery.

(2) Alcohol solvent process (Org. Synthesis, Coll., Vol. 1, 511)

This process also uses large quantities of alcohol (about 5 times) and hydrochloric acid (about 5 times) on the basis of the starting phenol and entails the same problems as mentioned above. Especially, this process is accompanied by difficult problems in the recovery of products. More specifically, the nitrosated product is normally very soluble in alcohol, and it is generally recovered in a solid form by diluting the reaction liquid with a large amount of water. Thus, there arise problems in the recoveries of both the nitrosated product itself and the alcohol.

(3) Aqueous solvent method (Ann. 277 85)

This process comprises causing an aqueous sulfuric acid solution to act on a dilute aqueous solution of a sodium salt of the starting phenol and sodium nitrite (wherein water is used in about 25-fold amount of the starting phenol). Water used as the solvent does not need to be recovered, but there exist significant problems in the efficiency per the volume of reactors and the recovery of product since the reaction is carried out in a very dilute system. The use of such a large amount of water is disadvantageous in that it is desirable from the viewpoint of preventing environmental pollution that the water used as the solvent be purified, although recovery of water is not necessary. If this reaction is carried out in a concentrated system, phenol, which has been formed as an intermediate in the course of the reaction, will be mixed with the nitrosated product in a pasty state, and the reaction will be discontinued.

(4) Nitrosation of dialkylanilines

One process of carrying out reaction uses a large amount (about 5-fold moles) of hydrochloric acid on the basis of the starting aniline in an aqueous solvent (Org. Synthesis, Coll. Vol. II, 223), and another process of carrying out reaction uses about 3-fold moles of hydrochloric acid, 2-fold moles of sodium nitrite and about 9-fold moles of acetic acid on the basis of the starting aniline [J. Chem. Soc., 1677 (1955)]. The products of these processes are in the form of the aniline hydrochloride, and an alkali treatment is required at the final stages of these reactions.

SUMMARY OF THE INVENTION

It is an object of the present invention to solve the above described problems in nitrosation processes. This object and other objects of the invention can be achieved by carrying out nitrosation in the presence of a relatively small amount of a specific organic acid or a salt thereof in an aqueous system of a relatively high concentration.

Thus, the process for nitrosation according to the present invention is characterized in that, in the preparation of the nitrosated products selected from the group consisting of benzoquinone oximes and p-nitroso-N,N-dialkylanilines which comprises subjecting the compounds to be nitrosated selected from the group consisting of phenols, N,N-dialkylanilines and mixtures thereof to nitrosation conditions using a nitrite ion in an aqueous system, the nitrosation reaction is carried out in the presence of an organic acid having pKa 2 to pKa 5 or a salt thereof and water, the quantities of the organic acid or a salt thereof and water being up to 5 times by mole and up to 10 times by weight the quantity of the compounds to be nitrosated, respectively. The organic acid and the salt thereof will hereinbelow be represented by the organic acid.

In accordance with the present invention, an increase in the efficiency per volume of reactors, facilitation of isolation and recovery of nitrosated products, elimination of the need for recovery of reaction media such as solvents, and enhancement of the yield of nitrosated products can be realized.

If the organic acids are not used in the process of the present invention, interactions between the nitrosated products and the starting phenols or anilines and by-products take place to form blackish brown lumps of the nitrosated product particles. Thus, both the yield and quality of the nitrosated product do not reach the intended levels. The role of the organic acids to be employed in the reaction of the present invention is considered to be that of a buffer to stabilize unstable nitrous acid, but the present invention should not be bound by such a theory. That the above described effects can be achieved by addition of such a small amount of the organic acids may be an unexpected result.

DETAILED DESCRIPTION OF THE INVENTION

1. Compounds to be nitrosated

The compounds to be nitrosated are phenols and N,N-dialkylanilines.

(1) Phenols

The compounds represented by the following general formula are satisfactorily employed in the present invention.

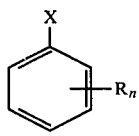

(1)

wherein: X is hydroxyl group; R is a lower alkyl group, a lower alkoxyl group, hydroxyl group, a di-lower-alkylamino group or a halogen (especially chlorine); and n is an integer of 0 to 4. In this case, the 4-position with reference to X of the ring is substituted with hydrogen. By the term "lower" group is meant a group containing up to about 5 carbon atoms. The term "a phenol" or "phenols" is thus to be understood as meaning the phenol derivatives of the formula (1) as well as phenol per se where n is zero in the formula (1).

Examples of such phenols are: (a) phenol (n=0); (b) mono-substituted phenols (n=1) such as o- and m-cresols, o- and m-ethylphenols, o- and m-propylphenols, o- and m-isopropylphenols, o- and m-butylphenols, o- and m-isobutylphenols, o- and m-tert-butylphenols, guaiacol, resorcinol, resorcinol mono-lower-alkyl ethers, o- and m-dimethylaminophenols, and o- and m-chlorophenols; (c) di-substituted phenols (n=2) such as thymol, 6-tert-butyl-o- and -m-cresols, pyrogallol, pyrogallol dimethyl ether, 2,3-dimethylphenol, 5- and 6-methyl-o- and -m-cresols, and 2,6-di-tert-buthyl-phenol; (d) tri-substituted phenols (n=3) such as 2,3,5- and 2,3,6-trimethylphenols, 5- and 6-methylpyrogallol, and 2,3-dimethoxy-5- and -6-methylphenols; (e) tetra-substituted phenols (n=4) such as 2,3,5,6-tetramethylphenol; (f) mixtures of the above-mentioned phenols, and mixtures of the above-mentioned phenol and the dialkylaniline enumerated below.

Among these phenols are typically employed phenol (n=0), o- or m-cresol, o- or m-chlorophenol, 2,3-dimethylphenol, 5-methyl-o-cresol, guaiacol, 2,3-dimethoxy-5- or -6-methylphenol, 6-tert-butyl-m-cresol, 6-tert-butyl-o-cresol, and 2,3,6-trimethylphenol. Phenol (n=0) and o-cresol are preferable.

(2) Dialkylanilines

The compounds represented by the following general formula are satisfactorily employed in the present invention.

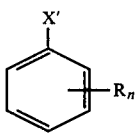

wherein, X' is a di-lower-alkylamino group, and the other designations are the same as those defined above with respect to the phenols. The di-lower-alkyl groups of the di-lower-alkylamino group (X') can be bonded together to form a ring with the nitrogen atom of the amino group.

Examples of such dialkylanilines are: N,N-dimethylaniline; N,N-diethylaniline; N,N-dimethyl-o- and -m- toluidines; mixtures of these dialkylanilines; and mixtures of the dialkylaniline and the above mentioned phenol. Among these compounds, typical di-alkylanilines are N,N-dimethylaniline and N,N-dimethyl-o-toluidine.

2. Nitrosation reaction

(1) Mode of reaction

By the term "nitrosation reaction conditions using a nitrite in an aqueous system" used herein is meant conditions under which an acid stronger than nitrous acid (hereinafter represented by a mineral acid) is caused to act on a nitrite ion in an aqueous medium to produce nitrous acid, and the compound to be nitrosated is then nitrosated with the resulting nitrous acid in the aqueous medium. It is to be understood that the above-mentioned formation in situ of nitrous acid from the nitrite ion and stronger acid is only an assumed reaction mechanism, and that what is important in the present invention is that the nitrosation reaction takes place in the presence of a nitrite ion and a mineral acid in an aqueous system.

One of the features of the present invention is that a suitable amount of the specified organic acid is present in the aqueous system. The process of the present invention can be carried out by optional modes of practice, including the use of the organic acids, as long as the effects of the present process can be realized.

In accordance with one of the preferred modes of practice, the total or a partial quantity of the organic acid is allowed to be present in an aqueous solution of the nitrite, ion and the mineral acid is slowly added to the reaction system. In this case, the compound to be nitrosated may be added in advance to the reaction system or slowly added together with the remaining quantity of the organic acid to the reaction system in proportion to the quantity of the mineral acid. It is generally preferred that the starting compound to be nitrosated be slowly added to the system. The total quantity of the compound to be nitrosated can be introduced to the reaction system especially when the compound is very soluble in an aqueous solution of the nitrite. The order of introducing the nitrite, the mineral acid, the organic acid, the compound to be nitrosated, and the aqueous medium into the reaction system is not restricted to the above described embodiments of the invention, but can be optionally combined provided that the reaction process can be carried out.

The aqueous system to be employed in the reaction system may consist solely of water, or may comprise a mixture of water and an organic solvent, preferably an organic solvent miscible with water (especially a polar solvent) such as a lower alcohol or glycol, di-oxane or dimethylformamide. The amount of the organic solvent is preferably less than that of water.

Any nitrite salt having nitrosating capability in the presence of a mineral acid in an aqueous system can be used as the nitrite, examples being ammonium salts, alkali metal salts, alkaline earth metal salts, and the salts of other metals. Representative nitrites are the alkali metal salts of nitrous acid. The acids to be employed in combination with such nitrites are the acids which are stronger than nitrous acid. Mineral acids such as sulfuric acid, hydrochloric acid, and phosphoric acid are typically employed. Sulfuric acid is preferably used, and a strong acid organic acid such as sulfonic acid can also be used. In this case, nitric acid is not preferred since nitration takes place simultaneously.

The nitrosation reaction proceeds with suitable stirring, and, after termination of the reaction, the resulting solid product is filtered to obtain the nitrosated product, generally with a purity of not lower than 90%. The solid product can be purified by conventional purification means such as recrystallization.

(2) Organic acids

The organic acids to be employed in a relatively small amount according to the present invention have pKa of from 2 to 5, and are generally carboxylic acids. Monocarboxylic acids are ordinarily used. The di- or tricarboxylic acids (especially dicarboxylic acids), which have the first dissociation constant pKa of from 2 to 5, can also be employed. The carboxylic acids can have non-hydrocarbyl substituents such as hydroxyl or a halo, e.g., chloro.

Such organic acids are exemplified by formic acid, acetic acid, propionic acid, butyric acid, isobutyric acid, malonic acid, succinic acid, malic acid, tartaric acid, glutaric acid, adipic acid, monochloroacetic acid, benzoic acid, valeric acid, toluic acid, and phthalic acid.

As indicated hereinabove, the term "organic acid" in construing the present invention includes a salt of the organic acid. Examples of salts include ammonium salt; alkali metal salts such as sodium or potassium salt; and alkaline earth metal salts such as magnesium, calcium or barium salt.

(3) Reaction conditions

The preferred reaction conditions are as set forth below. Of course, other reaction conditions can be used provided that the useful effects of the present invention are achieved.

| | |
|---|---|
| Reaction temperature | not higher than 50° C. |
| | preferably not higher than 20° C. |
| Reaction time | 1 to 24 hours |

(The time required for adding mineral acids slowly according to the above described preferred embodiment is about 1 to 22 hours, and the reaction time following the addition is about 0 to 2 hours.)

Quantities of ingredients to be used

| | |
|---|---|
| Ratio of nitrite to compound to be nitrosated | |
| | 1 to 5 (by equivalent) |
| | preferably 1 to 3 (by equivalent) |
| Ratio of mineral acid to compound to be nitrosated | |
| | 1 to 5 (by equivalent) |
| | preferably 1 to 3 (by equivalent) |
| Ratio of water to compound to be nitrosated | |
| | up to 10 (by weight) |
| | preerably 2 to 8 (by weight) |
| Ratio of organic acid to compound to be nitrosated | |
| | 0.001 to 5 (by mole) |
| | preferably not less than 0.005 (by mole) |

3. Nitrosation products

The process of the present invention produces 4-benzoquinone oximes from phenols and p-nitrosodialkylanilines from dialkylanilines. When diphenols or polyphenols are used as starting materials, only one hydroxyl group of the compounds generally undergoes nitrosation.

When the starting material is a benzene derivative having both a dialkylamino group and a hydroxyl group, only the hydroxyl group thereof generally undergoes nitrosation.

4. Experiments

EXAMPLE 1 (GENERAL OPERATION)

A 1-liter four-necked flask was equipped with a mechanical stirrer, a thermometer, and two dropping funnels. The flask was charged with 98 g (1.4 mol) of sodium nitrite and then 400 ml of water to dissolve the nitrite. The flask was cooled in an ice-water bath, and only 10 g (⅓ of the total quantity to be used) of acetic acid was added thereto. To the flask were added dropwise over 5 hours, with stirring, a mixture of 94 g (1.0 mol) of phenol and 20 g of acetic acid from one dropping funnel, and an aqueous sulfuric acid prepared by diluting 60 g (0.6 mol) of concentrated sulfuric acid to 110 ml from the other dropping funnel while the reaction temperature was kept at 15° C. or lower. Following the dropwise addition, the mixture was subjected to reaction for another 0.5 hour. The resulting solid product was filtered and washed twice with 600 ml of water to remove inorganic salts. The washing was followed by drying. The corresponding benzoquinone monooxime was obtained in a yield of 86%.

EXAMPLES 2 THROUGH 5 (ORGANIC ACID SPECIES)

The process of Example 1 was carried out with the use of the following organic acids in place of acetic acid. The results are shown in the following table together with that of Example 1.

| | Organic Acids | | |
|---|---|---|---|
| Examples | Species | Q'ty used g (mol) | Yield (%) |
| Example 1 | acetic acid | 30.0(0.5) | 86.0 |
| Example 2 | formic acid | 2.4(0.052) | 83.1 |
| Example 3 | propionic acid | 44.4(0.6) | 83.7 |
| Example 4 | butyric acid | 44.0(0.5) | 83.4 |
| Example 5 | malonic acid | 0.4(0.004) | 77.6 |

EXAMPLE 6

The process of Example 1 was carried out with the use of 108 g (1.0 mol) of o-cresol in place of phenol. As a result, 2-methylbenzoquinone-4-oxime was obtained in a yield of 84.7%.

EXAMPLE 7

In this example, 12.8 g (0.1 mol) of 2-chlorophenol was used. The reagents and solvent (water) were used in the same molar ratios as in Example 1. Reaction and post-treatment were carried out as in Example 1. Thus, 2-chlorobenzoquinone-4-oxime was obtained in a yield of 73.9%.

EXAMPLE 8

The process of Example 7 was repeated except that 6.2 g (0.05 mol) of guaiacol was used. As a result, 2-methoxybenzoquinone-4-oxime was obtained in a yield of 79.7%.

EXAMPLE 9

In this example, 4.8 g (0.04 mol) of N,N-dimethylaniline, and the reagents and solvent in the same molar ratios as in Example 1 were used. Reaction was carried out by dropwise addition for 2.5 hours and the post-reaction for 0.5 hour, followed by the same post-treatment as in Example 1. Thus, p-nitroso-N,N-dimethylaniline was obtained in a yield of 74.6%.

EXAMPLE 10

In this example, 8.2 g (0.05 mol) of 6-tert-butyl-m-cresol, the reagents in the same molar ratios as in Example 1, and a solvent consisting of 20 ml of water and 5 ml of isopropanol were used. Reaction and post-treatment were carried out as in Example 1. Thus, 2-tert-butyl-5-methylbenzoquinone-4-oxime was obtained in a yield of 82.9%.

EXAMPLE 11

The process of Example 10 was repeated except that 8.2 g (0.05 mol) of 6-tert-butyl-o-cresol was used. As a result, 2-tert-butyl-6-methylbenzoquinone-4-oxime was obtained in a yield of 89%.

EXAMPLE 12

In this example 1.36 g (0.01 mol) of 2,3,6-trimethylphenol and the reagents in the same molar ratios as in Example 3 were used. A mixture of the phenol and propionic acid was rendered into a liquid state by the addition thereto of 1 ml of dioxane. The procedure in Example 1 was carried with these materials, whereupon 2,3,6-trimethylbenzoquinone-4-oxime was obtained in a yield of 84.8%.

EXAMPLE 13

In this example 3.43 g (0.025 mol) of 3-dimethylaminophenol and the reagents in the same molar ratios as in Example 3 were used. A mixture of the phenol and propionic acid was rendered into a liquid state by the addition of 2.5 ml of methanol. The procedure in Example 1 was carried out, whereupon 3-N,N-dimethylaminobenzoquinone-4-oxime was obtained in a yield of 79.5%.

EXAMPLE 14

In this example 11 g (0.1 mol) of resorcinol and the reagents in the same molar ratios as in Example 1 were used. A mixture of resorcinol and acetic acid was rendered into an aqueous solution by addition of 10 ml of water. The procedure in Example 1 was carried out, whereupon 3-hydroxybenzoquinone-4-oxime was obtained in a yield of 72.6%.

What is claimed is:

1. In the process for the preparation of benzoquinone oxime compounds by subjecting a phenolic compound to nitrosation reaction conditions of nitrite ion in an aqueous system, the improvement which comprises: conducting said nitrosation reaction in the presence of an acid stronger than nitrous acid, an organic acid having a pKa of 2 to 5 and water, the quantities of the organic acid and water being up to 5 times by mole and up to 10 times by weight respectively the quantity of the compound to be nitrosated.

2. The process as set forth in claim 1, in which the phenolic compound is represented by the formula:

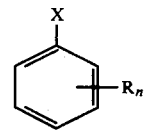

wherein X is a hydroxyl group; R is a lower alkyl group, a lower alkoxyl group, hydroxyl group, a di-lower-alkylamino group or a halogen; n is an integer of 0 to 4; the 4-position with respect to X of the rings being substituted with hydrogen.

3. The process as set forth in claim 2, in which the phenol is selected from the group consisting of phenol, o- or m-cresol, o- or m-ethylphenol, o- or m-propylphenol, o- or m-isopropylphenol, o- or m-butylphenol, o- or m-isobutylphenol, o- or m-tert-butylphenol, guaiacol, resorcinol, a resorcinol mono-lower-alkyl ether, o- or m-dimethylaminophenol, o- or m-chlorophenol, thymol, 6-tert-butyl-o- or -m-cresol, pyrogallol, pyrogallol dimethyl ether, 2,3-dimethylphenol, 5- or 6-methyl-o- or -m-cresol, 2,6-di-tert-butylphenol, 2,3,5- or 2,3,6-trimethylphenol, 5- or 6-methylpyrogallol, 2,3-dimethoxy-5- or -6-methylphenol, 2,3,5,6-tetramethylphenol, and mixtures thereof.

4. The process as set forth in claim 3, in which the phenol is phenol or o-cresol.

5. The process as set forth in claim 1, wherein the organic acid is a monocarboxylic acid or a dicarboxylic acid, said monocarboxylic acid and the first dissociation constant of said dicarboxylic acid having a pKa of 2 to 5.

6. The process as set forth in claim 5, in which the organic acid is selected from the group consisting of formic acid, acetic acid, propionic acid, butyric acid, isobutyric acid, malonic acid, succinic acid, malic acid, tartaric acid, glutaric acid, adipic acid, monochloroacetic acid, benzoic acid, valeric acid, toluic acid, phthalic acid, and mixtures thereof.

7. The process as set forth in claim 1, wherein the nitrosation reaction is conducted at a temperature of not greater than about 50° C. for about 1 to about 24 hours.

8. The process as set forth in any one of the preceding claims, wherein the organic acid is in the form of a salt.

9. The process as set forth in claim 8, wherein the salt is an ammonium, alkali metal, alkaline earth metal salt.

10. The process as set forth in claim 1, wherein to an aqueous nitrite solution comprising all or part of the organic acid are gradually added a mineral acid stronger than nitrous acid and the compound to be nitrosated together with the remaining organic acid.

11. The process as set forth in claim 1, wherein said quantity of the organic acid is 0.005 to 0.6 times by mole the quantity of the compound to be nitrosated.

* * * * *